US010064969B2

(12) United States Patent
Hsiao

(10) Patent No.: US 10,064,969 B2
(45) Date of Patent: Sep. 4, 2018

(54) LAMP-BASED AROMA DIFFUSER USING AN AROMA CAPSULE

(71) Applicant: Ming Jen Hsiao, Miaoli County (TW)

(72) Inventor: Ming Jen Hsiao, Miaoli County (TW)

( * ) Notice: Subject to any disclaimer, the term of this patent is extended or adjusted under 35 U.S.C. 154(b) by 51 days.

(21) Appl. No.: 15/258,757

(22) Filed: Sep. 7, 2016

(65) Prior Publication Data

US 2016/0375169 A1    Dec. 29, 2016

Related U.S. Application Data

(63) Continuation-in-part of application No. 14/157,302, filed on Jan. 16, 2014, now Pat. No. 9,500,358, and a continuation-in-part of application No. 14/042,162, filed on Sep. 30, 2013, now Pat. No. 9,498,553, said application No. 14/157,302 is a continuation-in-part of application No. 13/670,430, filed on Nov. 6, 2012, now Pat. No. 8,938,159, and a continuation-in-part of application No. 13/669,354, filed on Nov. 5, 2012, now Pat. No. 9,109,780, and a continuation-in-part of application No. 13/658,820, filed on Oct. 24, 2012, said application No. 14/042,162 is a continuation-in-part of application No. 13/658,820, filed on Oct. 24, 2012, and a continuation-in-part of application No. 13/549,493, filed on Jul. 15, 2012, and a continuation-in-part of application No.
(Continued)

(51) Int. Cl.
*F24F 6/00* (2006.01)
*A61L 9/03* (2006.01)
*F21V 33/00* (2006.01)
*F21V 17/10* (2006.01)
*F21V 1/14* (2006.01)

(52) U.S. Cl.
CPC ............... *A61L 9/03* (2013.01); *F21V 1/146* (2013.01); *F21V 17/104* (2013.01); *F21V 33/0028* (2013.01); *A61L 2209/133* (2013.01); *A61L 2209/135* (2013.01)

(58) Field of Classification Search
None
See application file for complete search history.

(56) References Cited

U.S. PATENT DOCUMENTS 949,606 A * 2/1910 Tetherow .............. A47J 27/004
165/135
1,431,719 A * 10/1922 Brown ................. H05B 3/0033
128/203.27
(Continued)

FOREIGN PATENT DOCUMENTS

EP    2679249 A1    1/2014

*Primary Examiner* — Thor Campbell
(74) *Attorney, Agent, or Firm* — Chun-Ming Shih

(57) ABSTRACT

A lamp-based aroma diffuser using an aroma capsule is disclosed to include a lamp housing, a hollow light-transmissive shade mounted in the lamp housing, a holder member mounted in the lamp housing, a heat conduction device mounted in the holder member, a heating element kept in contact with the bottom wall of the heat conduction device, a light-emitting device, and a power supply device-incorporated PC board for driving the heating element to heat the heat conduction device and a replaceable aroma diffuser in the heat conduction device and the light-emitting device to emit color light through the hollow light-transmissive shade and the lamp housing.

9 Claims, 6 Drawing Sheets

Related U.S. Application Data

13/549,490, filed on Jul. 15, 2012, now Pat. No. 8,668,885.

(56) References Cited

U.S. PATENT DOCUMENTS

| | | | | |
|---|---|---|---|---|
| 1,547,160 | A * | 7/1925 | Bailey | H05B 3/0033 119/73 |
| 2,043,647 | A * | 6/1936 | Berven | F24D 19/0082 261/119.1 |
| 2,742,342 | A * | 4/1956 | Dew | A01M 1/2083 392/391 |
| 2,881,303 | A * | 4/1959 | Resk | F24H 1/00 219/517 |
| 3,959,642 | A * | 5/1976 | Turro | A61L 9/03 362/92 |
| 4,544,592 | A * | 10/1985 | Spector | A61L 9/03 239/56 |
| 4,647,433 | A * | 3/1987 | Spector | A61L 9/03 206/390 |
| 4,781,895 | A * | 11/1988 | Spector | A01M 1/2088 261/DIG. 88 |
| 5,647,052 | A * | 7/1997 | Patel | A01M 1/2083 392/390 |
| 5,651,942 | A * | 7/1997 | Christensen | A61L 9/03 422/125 |
| 6,031,967 | A * | 2/2000 | Flashinski | A01M 1/2077 239/55 |
| 6,663,838 | B1 * | 12/2003 | Soller | A01M 1/2088 422/120 |
| 7,046,919 | B2 * | 5/2006 | Shimizu | A61L 9/03 392/390 |
| 7,670,566 | B2 * | 3/2010 | Adair | A01M 1/2077 239/34 |
| 8,047,837 | B2 * | 11/2011 | Furner | A61L 9/03 422/125 |
| 8,192,041 | B2 | 6/2012 | Hsiao | |
| 8,201,957 | B2 | 6/2012 | Hsiao | |
| 8,265,466 | B2 * | 9/2012 | Jorgensen | A61L 9/12 392/386 |
| 8,281,514 | B2 * | 10/2012 | Fleming | A01M 1/04 239/34 |
| 8,668,885 | B2 | 3/2014 | Witz | |
| 8,716,632 | B1 * | 5/2014 | Pesu | H05B 1/0269 219/433 |
| 8,765,073 | B1 | 7/2014 | Hsiao | |
| 8,787,739 | B2 | 7/2014 | Hsiao | |
| 8,983,277 | B2 | 3/2015 | Hsiao | |
| 9,028,759 | B2 | 5/2015 | Wirz | |
| 9,031,392 | B2 | 5/2015 | Hsiao | |
| 9,410,695 | B2 | 8/2016 | Hsiao | |
| 2005/0016985 | A1 * | 1/2005 | Haas | A61L 9/03 219/438 |
| 2005/0274818 | A1 * | 12/2005 | Ghazarian | A61L 9/02 239/34 |
| 2007/0014549 | A1 * | 1/2007 | Demarest | A61M 11/041 392/393 |
| 2007/0047931 | A1 * | 3/2007 | Niemeyer | A61L 9/03 392/390 |
| 2008/0013932 | A1 * | 1/2008 | He | A01M 1/2072 392/390 |
| 2011/0110824 | A1 | 5/2011 | Hsiao | |
| 2014/0110389 | A1 | 4/2014 | Hsiao | |
| 2015/0109823 | A1 | 4/2015 | Hsiao | |
| 2015/0117056 | A1 | 4/2015 | Hsiao | |

* cited by examiner

LAMP-BASED AROMA DIFFUSER USING AN AROMA CAPSULE

CROSS-REFERENCES TO RELATED APPLICATION

The present invention is a continuation-in-part of patent application Ser. No. 14/042,162 filed on Sep. 30, 2013 and Ser. No. 14/157,302 filed on Jan. 16, 2014.

BACKGROUND OF THE INVENTION

1. Field of the Invention

This invention relates to an aroma diffuser technology and more particularly, to a lamp-based aroma diffuser using an aroma capsule.

2. Description of Related Art

Various aroma diffusers are known. U.S. patent application Ser. Nos. 14/042,162 and 14/157,302 that were filed by the present inventor disclose similar designs. However, these designs have the disadvantages of labor and time consuming and complicated assembly process and increased production cost.

Further, regular lamps have the common disadvantage of casting a halo or shadow on the lamp housing when the internal light-emitting device is activated to emit light, obstructing the sense of beauty. More particularly, the design of a lamp-based aroma diffuser is focused on exquisite lighting atmosphere, the lighting quality must be optimally maintained.

Further, other aroma diffuser designs are seen in U.S. Pat. No. 8,066,402, U.S. Pat. No. 8,262,277, U.S. Pat. No. 8,147,116. However, after an application, the user must spend a lot of time to take the residual fragrant wax or essential oil out of the container, to clean the container and the aroma diffuser, and to refill a new fragrant wax or essential oil. This maintenance work is time and labor consuming. This drawback must be overcome.

SUMMARY OF THE INVENTION

The present invention has been accomplished under the circumstances in view. It is therefore the main object of the present invention to provides=a lamp-based aroma diffuser using an aroma capsule, which uses a disposable aroma capsule for releasing a pleasant smell and facilitates quick replacement of the disposable aroma capsule.

It is another object of the present invention to provide a lamp-based aroma diffuser using an aroma capsule, which enables the lamp housing to be lightened uniformly, creating a sense of beauty and avoiding casting a shadow over the lamp housing.

It is another object of the present invention to provide a lamp-based aroma diffuser using an aroma capsule, which significantly reduces the assembly cost and installation errors.

To achieve these and other objects of the present invention, a lamp-based aroma diffuser using an aroma capsule comprises a lamp housing, a hollow light-transmissive shade, a holder member, a heat conduction device and a heating element. The lamp housing comprises a first opening located on a top side thereof, and a second opening located on an opposing bottom side thereof. The hollow light-transmissive shade comprises a top edge and an opposing bottom edge. The hollow light-transmissive shade is mounted in the lamp housing to keep the top edge in the first opening of the lamp housing. The holder member comprises a top open side and a bottom hole. The holder member is mounted in the first opening of the lamp housing and supported on the top edge of the hollow light-transmissive shade. The heat conduction device is mounted at the bottom side of the holder member. The heating element is mounted in the bottom hole of the holder member, and kept in contact with the bottom wall of the heat conduction device. Further, the heating element is electrically coupled to a power supply unit for heating the heat conduction device.

When using the lamp-based aroma diffuser using an aroma capsule, the user can put an aroma capsule through the top open side of the holder member on the heat conduction device in of the holder member, and then turn on the power supply unit to activate the heating element, and thus, the generated heat energy is transferred from the heating element through the heat conduction device to the aroma capsule, causing the aroma capsule to release a fragrant vapor upwardly out of the top open side of the holder member.

In one embodiment of the present invention, the aroma diffuser further comprises a power supply device, a PC board, a light-emitting device, and a light-diffusing lampshade mounted in the hollow light-transmissive shade. The power supply device can be, for example, a DC socket electrically coupled with the PC board, the heating element and the light-emitting device. The PC board controls the on/off operation of the power supply device, the heating element and the light-emitting device. The light-emitting device can be a LED or lamp bulb electrically connected to and mounted on the PC board. The light-diffusing lampshade covers the light-emitting device, enabling the light emitted by the light-emitting device to be uniformly diffused through the hollow light-transmissive shade and the lamp housing so that the lamp housing can be lightened uniformly, creating a sense of beauty and avoiding casting a shadow over the lamp housing and avoiding casting a shadow on the lamp housing. In this embodiment, the lamp housing is a lantern housing; the PC board controls the light-emitting device to emit a color light, for example, red light onto the hollow light-transmissive shade toward the lamp housing. Thus, the aroma diffuser of the present invention works as an electric lantern to create an atmosphere of red luster beauty while releasing a pleasant smell.

Preferably, the hollow light-transmissive shade and light-diffusing lampshade are selected from translucent materials, semi-transparent materials, colored transparent materials or materials having a high surface heat transfer coefficient, such as color glass, acrylic or plastic materials, frosted plastic, glass or acrylic materials, or materials with fine scribed lines. The colored transparent materials are capable of enabling the light emitted by the light-emitting device to be uniformly diffused through the light-diffusing lampshade and the hollow light-transmissive shade, avoiding casting a shadow over the lamp housing.

Preferably, the holder member further comprises a positioning block and an engagement block spaced around the periphery of the holder member. The hollow light-transmissive shade 的 top edge comprises a positioning groove and an engagement hole respectively disposed corresponding to the positioning block and the engagement block. Thus, the positioning block can be easily guided into the positioning groove, enabling the engagement block to be rapidly and accurately engaged into the engagement hole to assure a foolproof installation.

When compared with the prior art design, the lamp-based aroma diffuser using an aroma capsule provides a special structural design, which facilitates quick installation to reduce the assembly cost and installation errors, is capable of releasing a pleasant small and generating lighting effects, and enables the lamp housing can be lightened uniformly, creating a sense of beauty and avoiding casting a shadow over the lamp housing.

BRIEF DESCRIPTION OF DRAWINGS

The invention can be more fully understood by reading the following detailed description of the preferred embodiments, with reference made to the accompanying drawings, wherein.

DETAILED DESCRIPTION OF THE INVENTION

Figure 1:
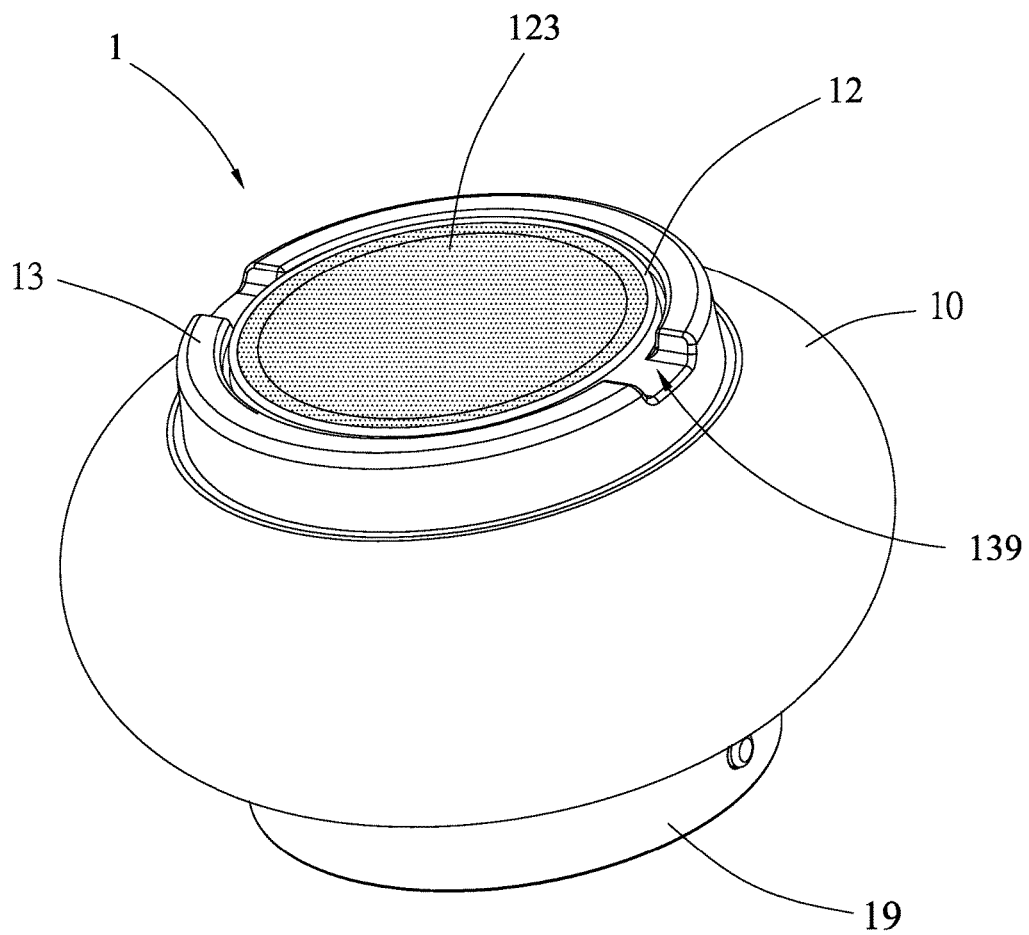
FIG. 1 is an oblique top elevational view of a lamp-based aroma diffuser using an aroma capsule in accordance with the present invention.
Figure 2A:
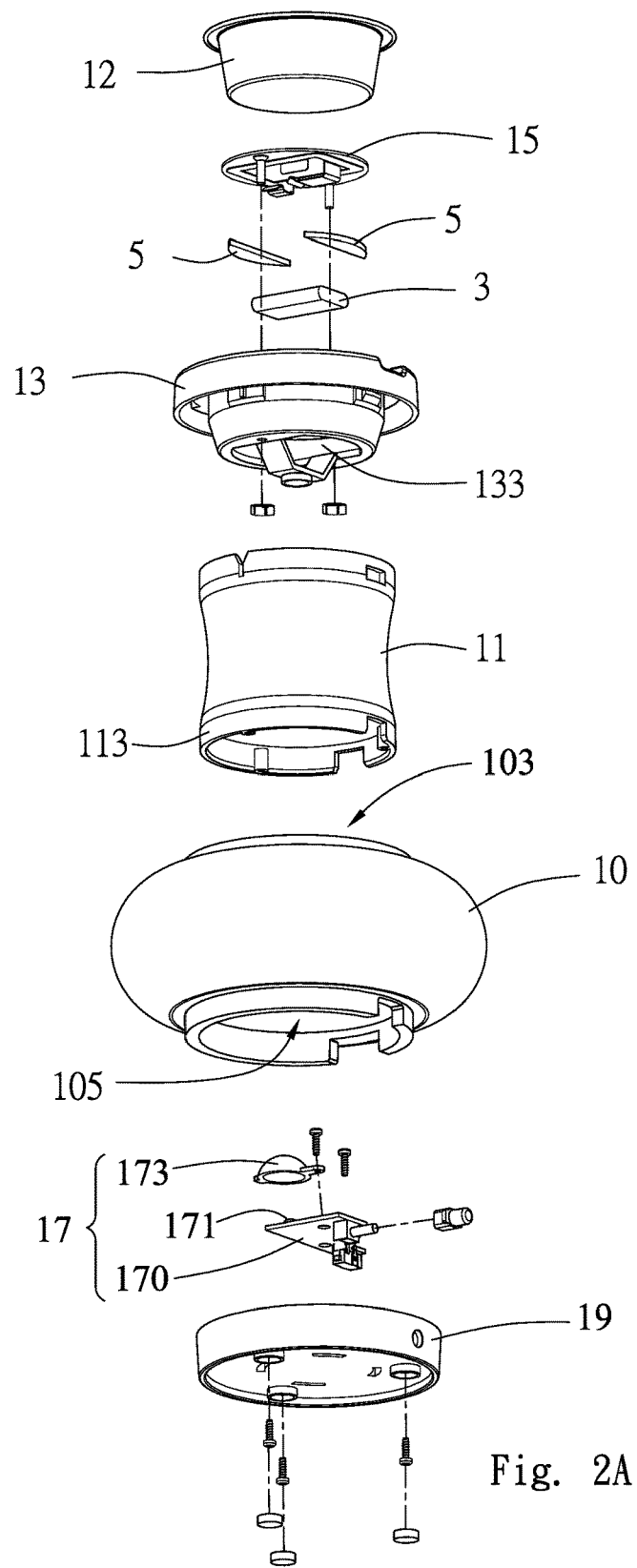
FIG. 2A is an exploded view of the lamp-based aroma diffuser using an aroma capsule in accordance with the present invention.
Figure 2B:
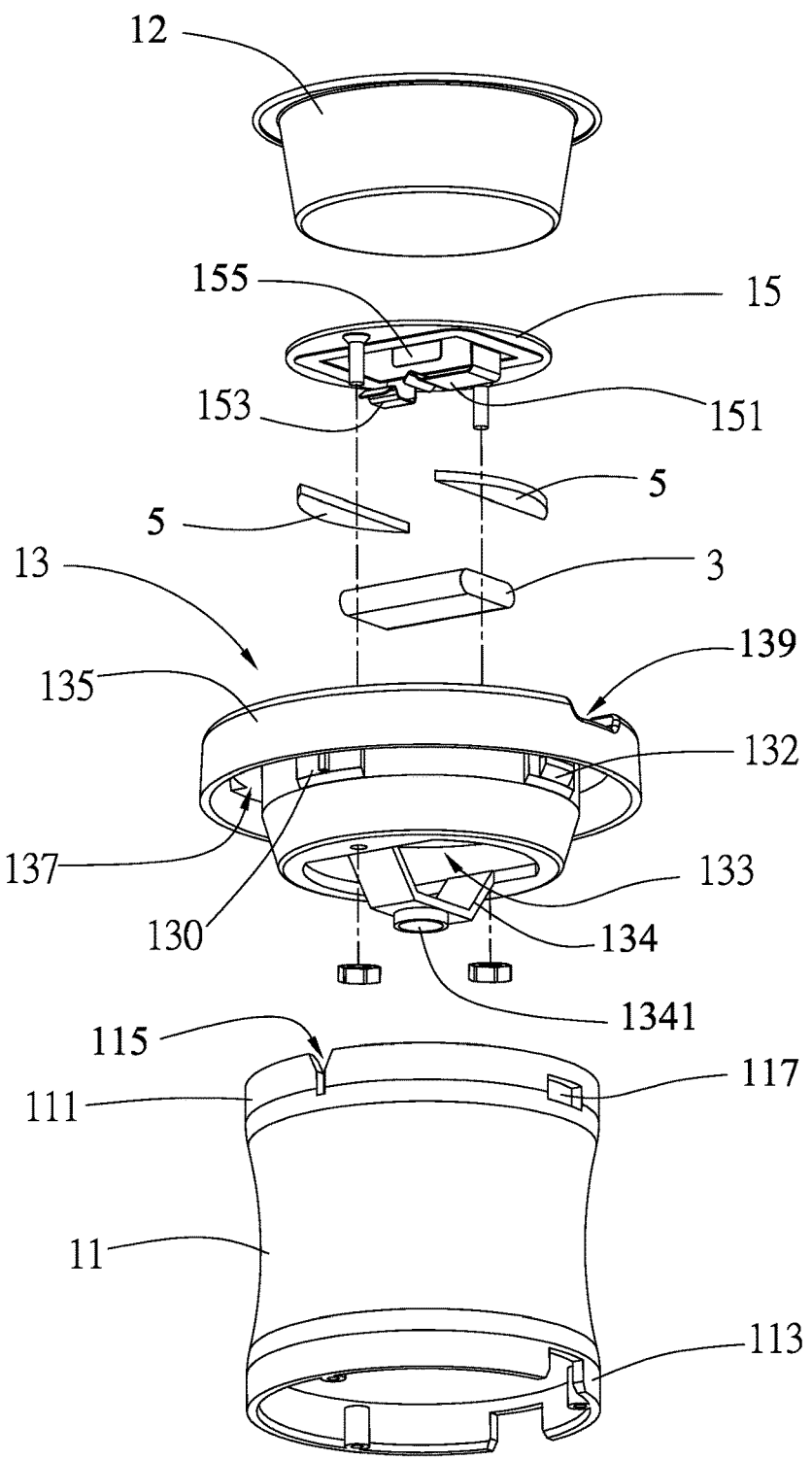
FIG. 2B is an enlarged view of a part of FIG. 2A.
Figure 3:
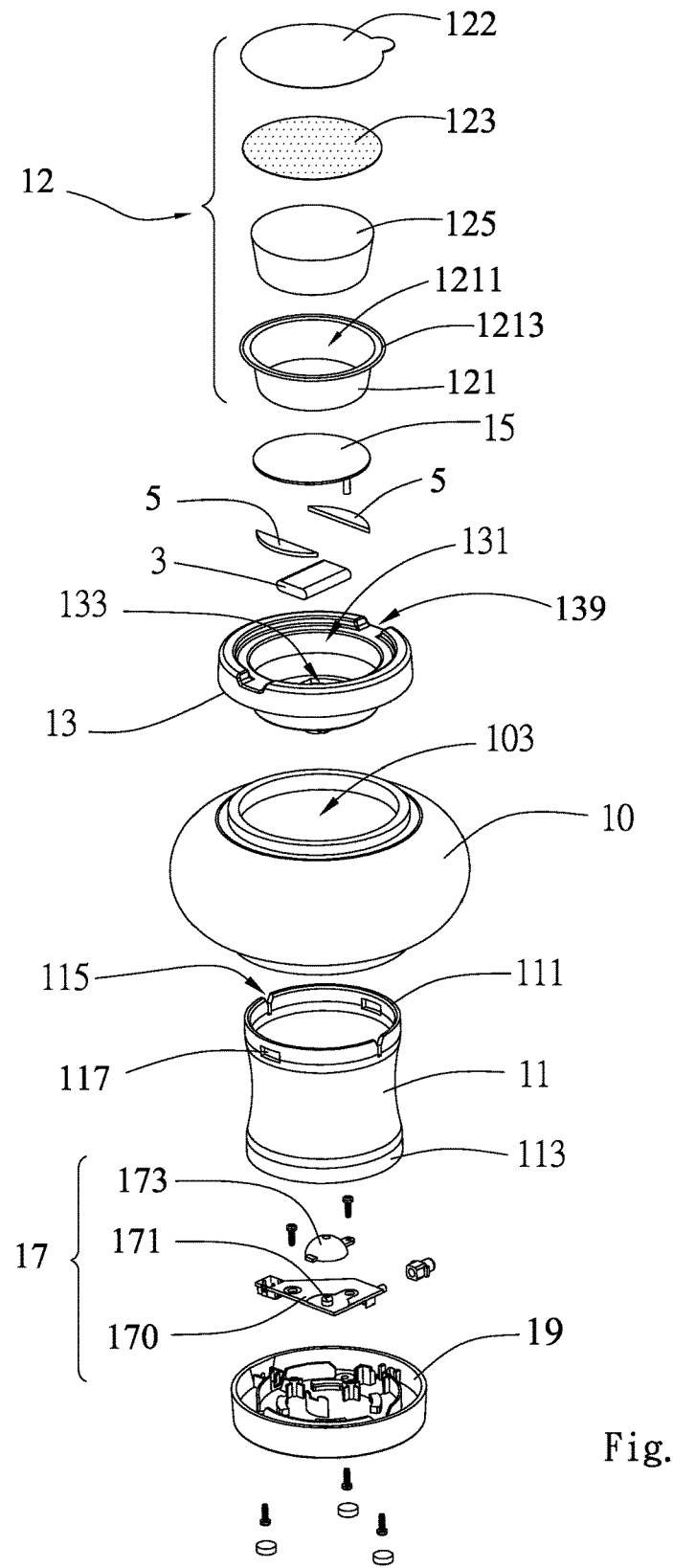
FIG. 3 is another exploded view of the lamp-based aroma diffuser using an aroma capsule in accordance with the present invention.
Figure 4:
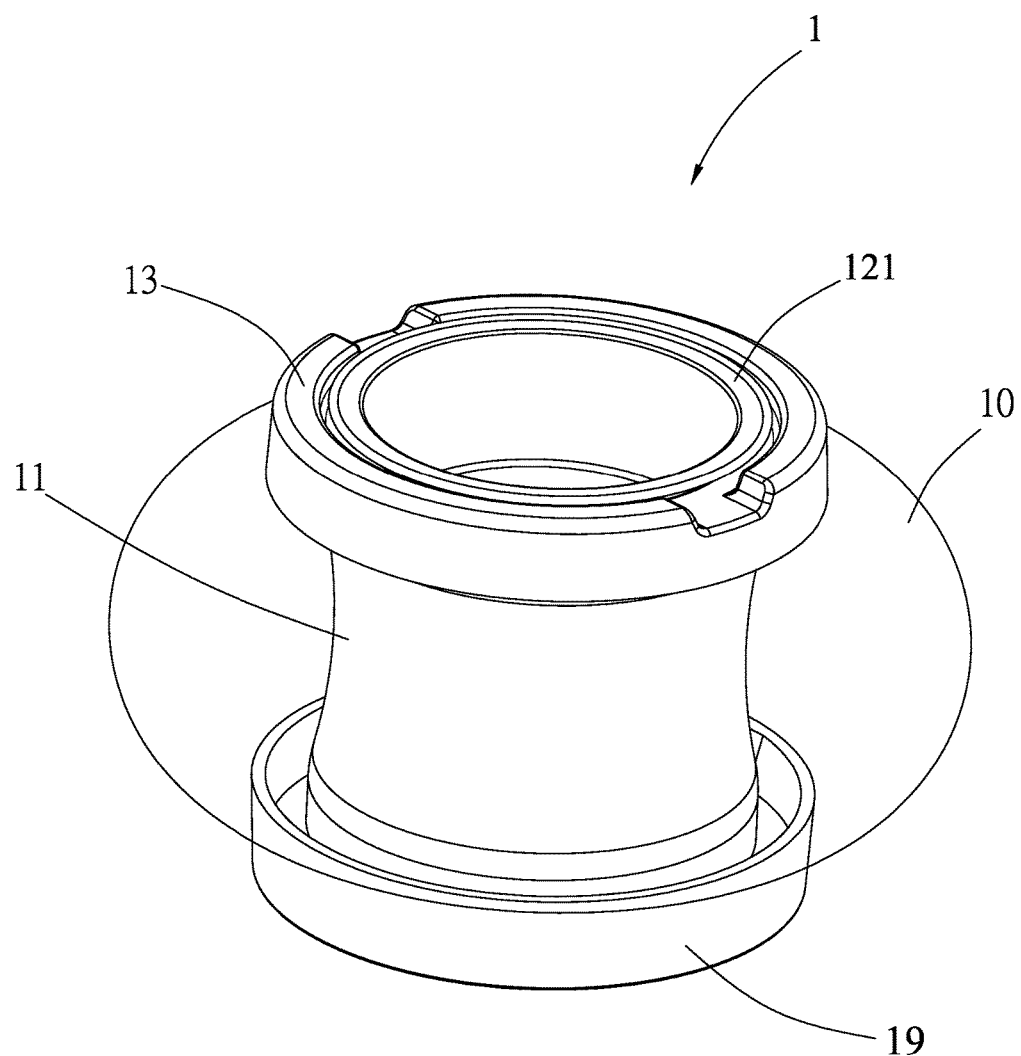
FIG. 4 is a perspective view illustrating the arrangement of the hollow light-transmissive shade and the lamp housing.

Referring to FIGS. 1-5, a lamp-based aroma diffuser using an aroma capsule 1 in accordance with the present invention is shown. The lamp-based aroma diffuser using an aroma capsule 1 comprises a lamp housing 10, a hollow light-transmissive shade 11, a holder member 13, a heat conduction device 15 and a heating element 3. The lamp housing 10 defines a first opening 103 on one side, namely the top side thereof, and a second opening 105 on an opposite side, namely, the bottom side thereof. The hollow light-transmissive shade 11 comprises a top edge 111 located on a top side thereof, and a bottom edge 113 located on an opposing bottom side thereof. The hollow light-transmissive shade 11 is mounted inside the lamp housing 10 with the top edge 111 fitted into the first opening 103. The holder member 13 comprises a top open side 131, and an opposing bottom hole 133. The holder member 13 is fastened to the first opening 101 of the lamp housing 10 and the top edge 111 of the hollow light-transmissive shade 11. The heat conduction device 15 is mounted at a bottom side inside the holder member 13. The heating element 3 is mounted in the bottom hole 133 of the holder member 13, and kept in contact with the bottom wall of the heat conduction device 15, The heating element 3 is electrically connected to a power supply unit (not shown), and adapted for heating the heat conduction device 15 of the aroma diffuser 1.

When using the lamp-based aroma diffuser using an aroma capsule 1, the user can put an aroma capsule 12 through the top open side 131 into the inside of the holder member 13. After the heating element 3 is electrically connected to the power supply unit (not shown) and electrically conducted, the heating element 3 generates heat to heat the heat conduction device 15, thereby melting the aroma capsule 12 to release a fragrant vapor upwardly out of the top open side 131 of the holder member 13.

As illustrated in FIGS. 2A, 2B, 3, 4 and 5, the aroma diffuser 1 further comprises a power supply device 17, a PC board 170, a light-emitting device 171, and a light-diffusing lampshade 173 mounted in the hollow light-transmissive shade 11. The power supply device 17 can be, for example, a DC socket electrically coupled with the PC board 170, the heating element 3 and the light-emitting device 171. The PC board 170 controls the on/off operation of the power supply device 17, the heating element 3 and the light-emitting device 171. The light-emitting device 171 can be a LED or lamp bulb electrically connected to and mounted on the PC board 170. The light-diffusing lampshade 173 covers the light-emitting device 171, enabling the light emitted by the light-emitting device 171 to be uniformly diffused through the hollow light-transmissive shade 11 and the lamp housing 10 so that the lamp housing 10 can be lightened uniformly, creating a sense of beauty and avoiding casting a shadow over the lamp housing 10.

In the present preferred embodiment, the lamp housing 10 is a lantern housing; the PC board 170 controls the light-emitting device 171 to emit a color light, for example, red light onto the hollow light-transmissive shade 11 toward the lamp housing 10. Thus, the aroma diffuser 1 of the present invention works as an electric lantern to create an atmosphere of red luster beauty while releasing a pleasant smell.

Referring to FIGS. 2A and 3-5 again, the aroma diffuser 1 further comprises a bottom cover 19 fastened to the second opening 105 of the lamp housing 10 to hold the power supply device 17, the PC board 170 and the bottom cover 19 in the lamp housing 10.

The aforesaid hollow light-transmissive shade or light-diffusing lampshade can be selected from translucent materials, semi-transparent materials, colored transparent materials or materials having a high surface heat transfer coefficient, such as color glass, acrylic or plastic materials, frosted plastic, glass or acrylic materials, or materials with fine scribed lines. The colored transparent materials for making the light-diffusing lampshade 173 or the hollow light-transmissive shade 11 can be of gray, amber, red or milky color that are capable of enabling the light emitted by the light-emitting device 171 to be uniformly diffused through the light-diffusing lampshade 173 and the hollow light-transmissive shade 11, avoiding casting a shadow over the lamp housing 10.

Referring to FIGS. 2A, 2B, 4 and 5 again, in one embodiment of the present invention, the holder member 13 further comprises a flange 135 and an annular groove 137. The flange 135 extends downwardly from the top side of the holder member 13, defining with the upper part of the outer perimeter of the holder member 13 the said annular groove 137. The holder member 13 is mounted on the lamp housing 10 and the hollow light-transmissive shade 11 by forcing the annular groove 137 into engagement with the top edge of the lamp housing 10 and the top edge of the hollow light-transmissive shade 11.

Referring to FIGS. 2A, 2B and 5 again, in one embodiment of the present invention, the holder member 13 further comprises a positioning block 130 and an engagement block 132. The positioning block 130 and the engagement block 132 are spaced around the periphery of the holder member 13. The hollow light-transmissive shade 11 further comprises a positioning groove 115 and an engagement hole 117 located on the top edge 111 and respectively disposed corresponding to the positioning block 130 and the positioning block 130. Thus, the positioning block 130 can be easily inserted into the positioning groove 115, enabling the engagement block 132 to be rapidly and accurately engaged into the engagement hole 117 to assure a foolproof installation.

As illustrated in the annexed drawings, the positioning block 130 is a rectangular block; the engagement block 132 is a trapezoidal block; the positioning groove 115 is a Y-shaped groove located on the top edge 111 gradually reduced in width from the top side toward the opposing bottom side; the engagement hole 117 is a rectangular hole. When assembling the holder member 13 with the hollow light-transmissive shade 11 and the lamp housing 10, the wide top and narrow bottom characteristic of the Y-shaped design of the positioning groove 115 enables the positioning block 130 to be inserted into the positioning groove 115 easily to assure a foolproof installation. At the same time, the engagement block 132 can be accurately engaged into the engagement hole 117 and, the annular groove 137 of the holder member 13 can be rapidly and accurately forced into engagement with the top edge of the lamp housing 10 and the top edge of the hollow light-transmissive shade 11.

Referring to FIGS. 1-3 again, in one embodiment of the present invention, the holder member 13 further comprises an operating notch 139 located on the top edge thereof. In the present preferred embodiment, the operating notch 139 is located on the top side of the flange 135. After the aroma capsule 12 is used out, the user can insert the fingers through the operating notch 139 to take the used aroma capsule 12 out of the holder member 13 conveniently. On the contrary, the user can insert the fingers through the operating notch 139 to put a new aroma capsule 12 into the holder member 13 rapidly.

Referring to FIGS. 2A, 2B and 5 again, in one embodiment of the present invention, the holder member 13 further comprises a lead frame 134. The lead frame 134 defines therein a wire hole 1341. The lead frame 134 is located at the bottom side of the holder member 13. The wire hole 1341 is spaced below the bottom hole 133 and kept in axial alignment with the bottom hole 133. The heating element 3 is electrically bonded with an electrical wire (not shown) that is inserted through the wire hole 1341 and electrically connected to the power supply device 17 and the PC board 170 in the hollow light-transmissive shade 11. By means of the wire hole 1341, the electrical wire is kept at the axial center in the hollow light-transmissive shade 11, so that the shadow of the light-emitting device 171 will not be casted on the lamp housing 10, maintaining the sense of beauty of the aroma diffuser.

Referring to FIGS. 1-5 again, in one embodiment of the present invention, the heat conduction device 15 comprises a first locating plate 151 disposed in the bottom hole 133. In the present preferred embodiment, the first locating plate is an L-shaped spring plate. The first locating plate 151 has one end thereof fastened to the bottom side of the heat conduction device 11, and an opposite end thereof freely suspended for holding the heating element 3 in contact with the bottom surface of the heat conduction device 15. The heat conduction device 15 further comprises a second locating plate 153 disposed in the bottom hole 133. In the present preferred embodiment, the second locating plate 153 is an L-shaped spring plate. The second locating plate 153 has one end thereof fastened to the bottom side of the heat conduction device 11, and an opposite end thereof freely suspended in a perpendicular manner relative to the first locating plate 151 for securing the heating element 3 in another direction.

Figure 5:
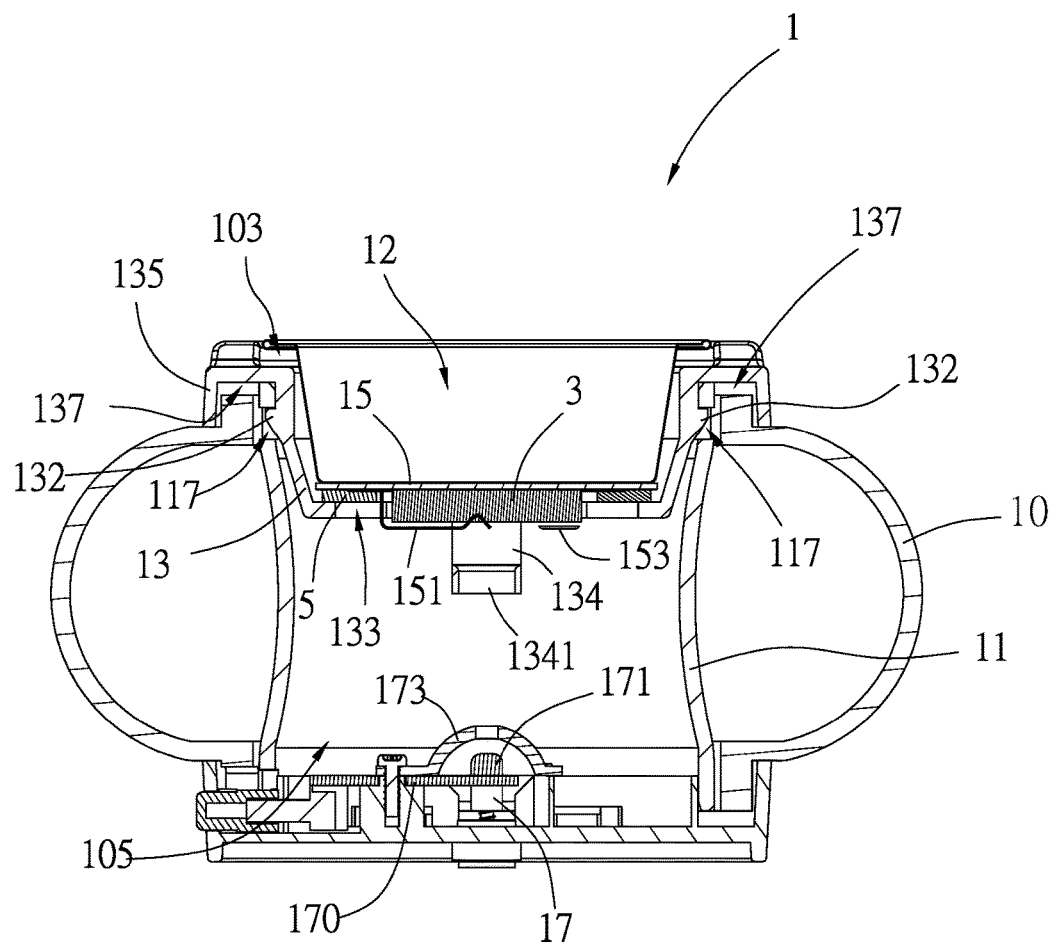
FIG. 5 is a sectional assembly view of the lamp-based aroma diffuser using an aroma capsule in accordance with the present invention.

Referring to FIGS. 2 and 5, the heat conduction device 15 further comprises a stop plate 155 downwardly extended from the bottom side thereof and disposed at one lateral side relative to the first locating plate 151 and the second locating plate 153 for stopping the heating element 3 at the bottom side of the heat conduction device 15.

The aroma diffuser 1 further comprises at least one, for example, two heat insulation pads 5 mounted between the bottom side of the heat conduction device 15 and the inner bottom side of the holder member 13 to prevent the transfer of heat energy from the heat conduction device 15 to the holder member 13.

Referring to FIGS. 2A, 2B and 5 again, the lamp-based aroma diffuser using an aroma capsule 1 is used with an aroma capsule 12. The aroma capsule 12 is placed on the heat conduction device 15 inside the holder member 13. The aroma capsule 12 further comprises a disposable container 121 and an aroma 125. The disposable container 121 comprises an opening 1211 and a protruding edge 1213. The protruding edge 1213 extends outward from the opening 1211. The protruding edge 1213 allows the user to move and operate the aroma capsule 12 easily and conveniently. The aroma 125 is contained in the disposable container 121. The aroma 125 is, for example, a scented wax, essential oil, flavor block or fragrance stone. In the present preferred embodiment, the aroma 125 is a scented wax. Thus, when electrically conducted, the heating element 3 generates heat to heat the heat conduction device 15 in the holder member 13, thereby melting the aroma 125 to release a pleasant smell.

Referring to FIG. 5 and FIGS. 2 and 3 again, in the present preferred embodiment, the aroma capsule 12 further comprises a breathing film 123 sealed to the opening 1211 of the disposable container 121 to stop the melted scented wax or aroma from flowing out of the aroma capsule, assuring safety.

The foregoing descriptions of the detailed embodiments are only illustrated to disclose the features and functions of the present invention and not restrictive of the scope of the present invention. It should be understood to those in the art that all modifications and variations according to the spirit and principle in the disclosure of the present invention should fall within the scope of the appended claims.

What is claimed is:

1. A lamp-based aroma diffuser using an aroma capsule, comprising a lamp housing comprising a first opening located on a top side thereof and a second opening located on an opposing bottom side thereof, a hollow light-transmissive shade mounted in said lamp housing and comprising a top edge disposed in said first opening of said lamp housing and an opposing bottom edge, a holder member mounted in said first opening of said lamp housing, said holder member comprising a top open side and a bottom hole, a heat conduction device mounted in said holder member and a heating element kept in contact with a bottom wall of said heat conduction device and electrically connectable to a power supply unit for heating said heat conduction device to melt an aroma diffuser in said heat conduction device, wherein an upper surface of the holder member is concaved to form at least one operating notch for allowing a user's finger to lift the aroma capsule.

2. The lamp-based aroma diffuser using an aroma capsule as claimed in claim 1, further comprising a power supply device, a PC board, a light-emitting device, and a light-diffusing lampshade mounted in said hollow light-transmissive shade, said power supply device being electrically coupled with said PC board, said heating element and said light-emitting device, said PC board being adapted for controlling the on/off operation of said power supply device, said heating element and said light-emitting device, said light-emitting device being mounted on and electrically connected to said PC board, said light-diffusing lampshade surrounding said light-emitting device.

3. The lamp-based aroma diffuser using an aroma capsule as claimed in claim 1, wherein said hollow light-transmissive shade and said light-diffusing lampshade are selected from the group of translucent materials, semi-transparent materials, colored transparent materials and materials having a high surface heat transfer coefficient.

4. The lamp-based aroma diffuser using an aroma capsule as claimed in claim 2, wherein said hollow light-transmissive shade and said light-diffusing lampshade are selected from the group of translucent materials, semi-transparent materials, colored transparent materials and materials having a high surface heat transfer coefficient.

5. The lamp-based aroma diffuser using an aroma capsule as claimed in claim 2, further comprising a bottom cover fastened to said second opening of said lamp housing to hold said power supply device and said PC board in said lamp housing.

6. The lamp-based aroma diffuser using an aroma capsule as claimed in claim 1, wherein said holder member further comprises a flange downwardly extended from a top edge and surrounding the periphery of said holder member, and an annular groove defined between said flange and the periphery of said holder member and fastened to a top edge of said lamp housing and the said top edge of said hollow light-transmissive shade.

7. The lamp-based aroma diffuser using an aroma capsule as claimed in claim 6, wherein said holder member further comprises a positioning block and an engagement block spaced around the periphery thereof; said hollow light-transmissive shade comprises a positioning groove and an engagement hole located on the top edge thereof and respectively disposed corresponding to said positioning block and said engagement block, said positioning groove being adapted for guiding in said positioning block for enabling said engagement block to be accurately engaged into said engagement hole.

8. The lamp-based aroma diffuser using an aroma capsule as claimed in claim 7, wherein said positioning block is a rectangular block; said engagement block is a trapezoidal block; said positioning groove is a Y-shaped groove located on the said top edge of said hollow light-transmissive shade and gradually reduced in width from a top side toward an opposing bottom side for guiding in said positioning block for enabling said engagement block to be accurately engaged into said engagement hole.

9. The lamp-based aroma diffuser using an aroma capsule as claimed in claim 1, wherein said holder member further comprises a lead frame located at a bottom side thereof, said lead frame comprising a wire hole spaced below said bottom hole in an axial alignment manner.

\* \* \* \* \*